United States Patent [19]
Chang

[11] Patent Number: 5,799,326
[45] Date of Patent: Sep. 1, 1998

[54] SUN-VISORS

[76] Inventor: Kuei-Sen Liao Chang, No. 231, Ta Yeh Rd., Taichung, Taiwan

[21] Appl. No.: 968,624

[22] Filed: Nov. 12, 1997

[51] Int. Cl.$^6$ .................................................. A61F 9/00
[52] U.S. Cl. .................................. 2/12; 2/200.3; 2/209.3
[58] Field of Search ........................... 2/12, 171, 200.3, 2/209.3, 209.4

[56] References Cited

U.S. PATENT DOCUMENTS 2,474,507  6/1949  Wolfe ............................... 2/209.3

*Primary Examiner*—Diana Biefeld
*Attorney, Agent, or Firm*—Kirkpatrick & Lockhart LLP

[57] ABSTRACT

A sun-visor includes a first plate having a curved inner side from which a second plate extends. A curved slit is defined along an outer side of the first plate so as to form a curved fastening member foldably connected to two ends of the first plate. A belt is connected to two sides of the second plate.

2 Claims, 4 Drawing Sheets

SUN-VISORS

BACKGROUND OF THE INVENTION

1. Field of the Invention

The present invention relates to a type of headgear and, more particularly, to a sun-visor having a peak with a decorative plate extending from the peak and a fastening member connected between two ends of the peak.

2. Brief Description of the Prior Art

Sun visors are a particularly popular form of headgear as they are not expensive to manufacture and so an excellent promotional medium, are easily adapted to different sizes of heads and provide shade to eyes without blocking heat dissipation of a head. FIG. 1 shows a conventional sunvisor which is commonly seen in situations such as a baseball game. The sun-visor includes a peak 10 having a board 11 extending upwardly from an upper side thereof and two fastening members 12 respectively extending from a respective one of two ends of the peak 10. The two fastening members 12 each have an engaging member (not shown) disposed to a distal end thereof so as to connect the two fastening members 12 together to mount the sun-visor on a wearer's head. Because such sun-visors have a simple structure and are cheap, the peak 10 and the board 11 are often used to achieve commercial purposes, i.e. display a logo etc. However, as all the sun-visors have a similar structure and the same manner of usage, the conventional sun-visor as become mundane and unattractive. Furthermore, the peak 10, the board 11 and the fastening members 12 need to be manufactured separately which increases manufacturing cost of the sun-visor.

The present invention intends to provide an improved sun-visor to mitigate and/or obviate the above-mentioned problems.

SUMMARY OF THE INVENTION

The present invention provides a sun-visor which includes a first plate having a curved inner side and a second plate extending from the curved inner side of the first plate. A slit is defined near an outer side of the first plate so as to form a curved fastening member foldably connected to two ends of the first plate. A belt is connected to two sides of the second plate.

It is an object of the present invention to provide a sun-visor having a fastening member connected to a peak thereof to mount the sun-visor to a wearer's head and a belt connected to a decorative plate extending from the peak of the sun-visor.

It is another object of the present invention to provide a sun-visor having a decorative plate which is used as a mask.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
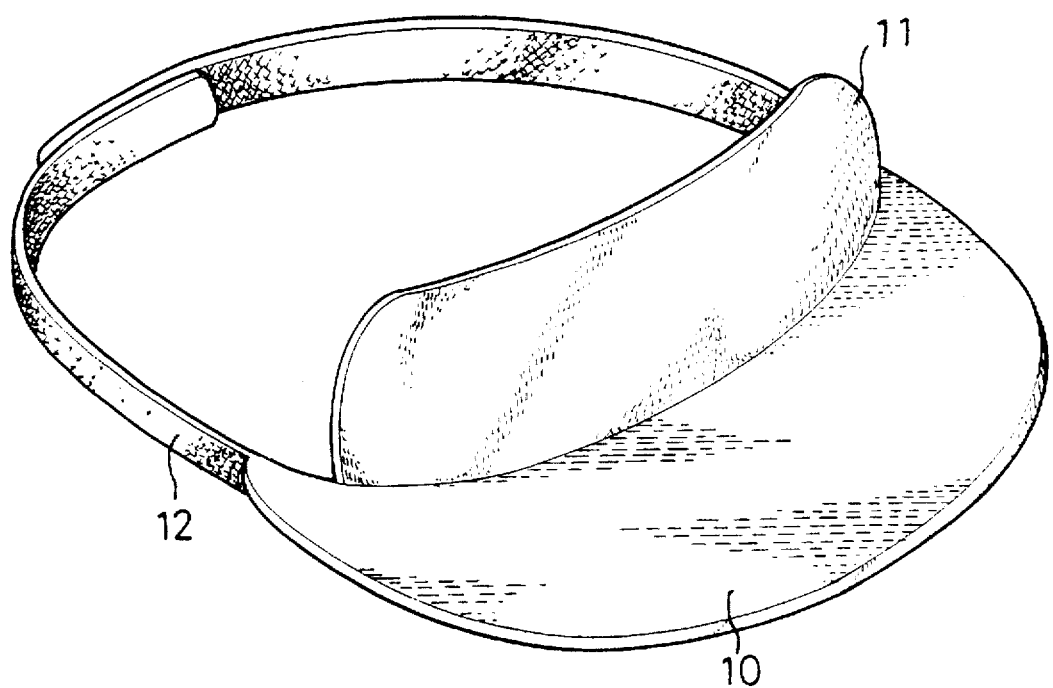
FIG. 1 is a perspective view of a conventional sun-visor.
Figure 2:
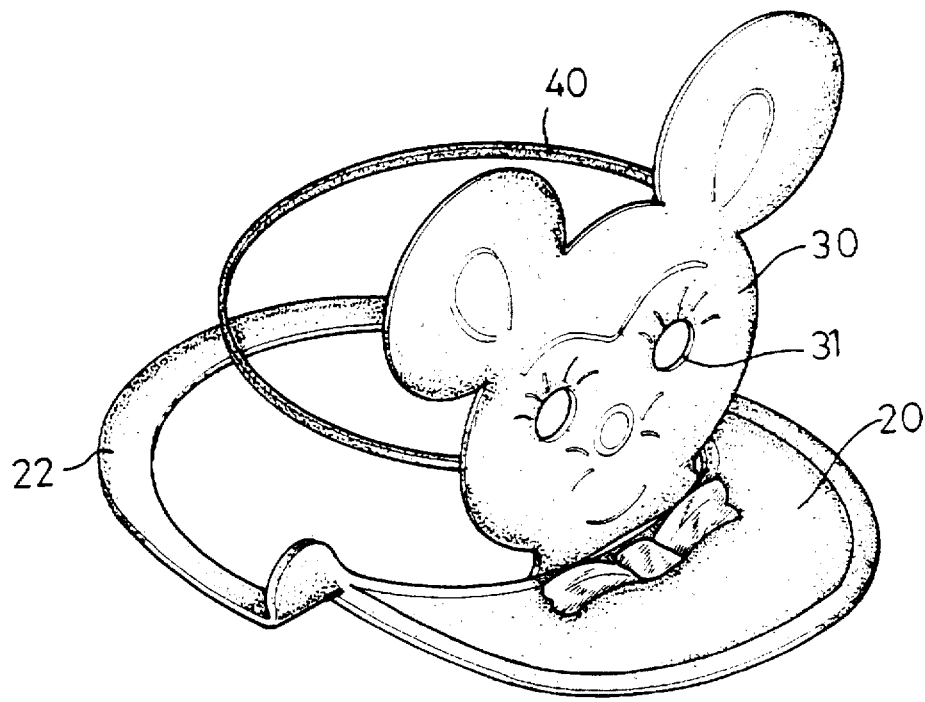
FIG. 2 is a perspective view of a sun-visor in accordance with the present invention.
Figure 3:
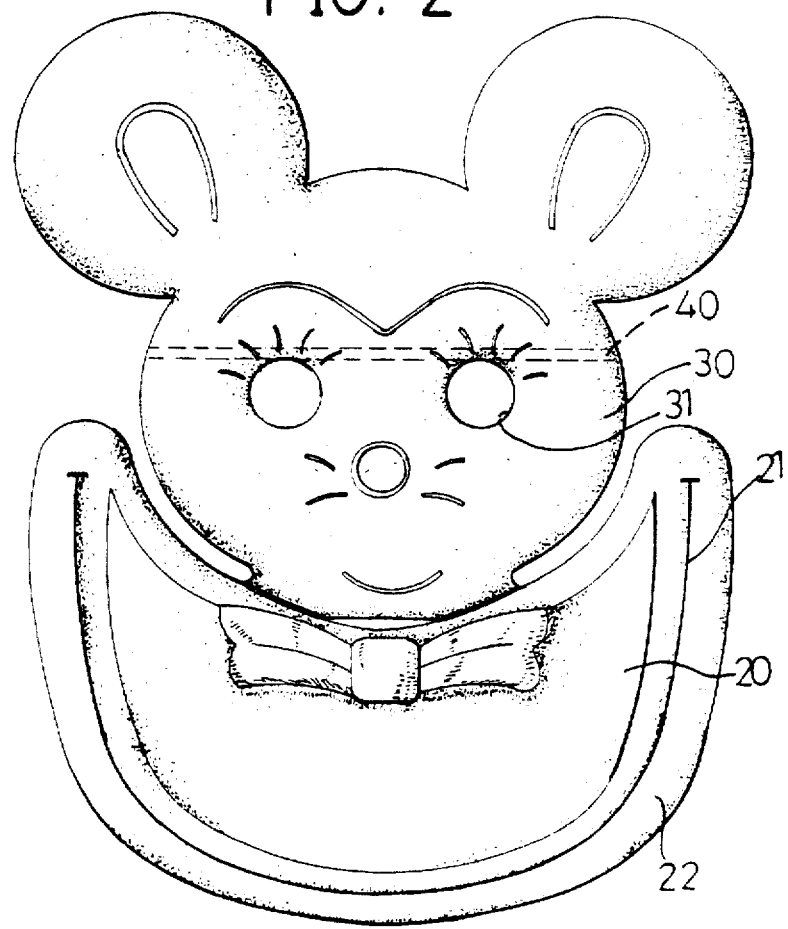
FIG. 3 is an elevational view of the sun-visor when a fastening member is not yet folded away from a peak thereof.

Referring to the drawings and initially to FIGS. 2 and 3, a sun-visor in accordance with the present invention generally includes a first plate 20 having a curved inner edge and a curved slit 21 defined therethrough near an outer edge thereof. The outer edge can be partly separated from the first plate 20 along the curved slit and swung approximately 180° from the first plate 20 to form a fastening member 22. The fastening member 22 is foldably connected to two ends of the first plate 20 as shown in FIG. 2. A second plate 30 extends from the curved inner side of the first plate 20 and has two holes 31 defined therethrough. A belt 40 is connected to two sides of the second plate 30.

Figure 4:
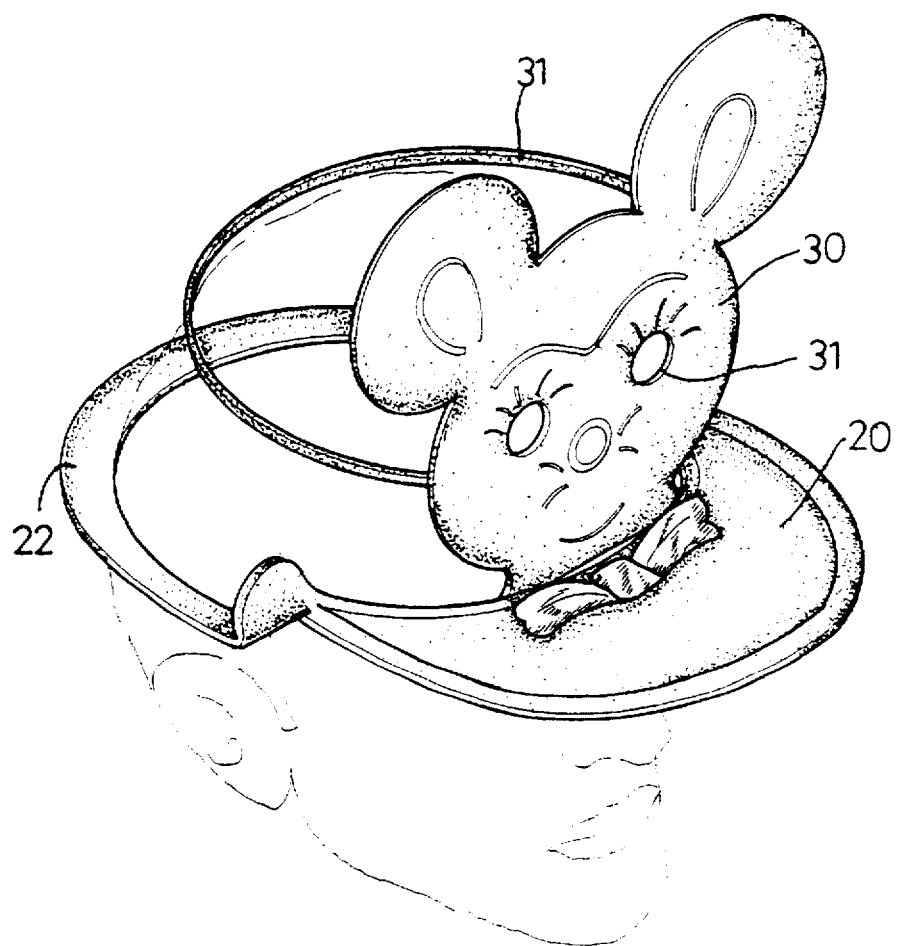
FIG. 4 is an illustrative view to show the sun-visor is mounted to a wearer's head.
Figure 5:
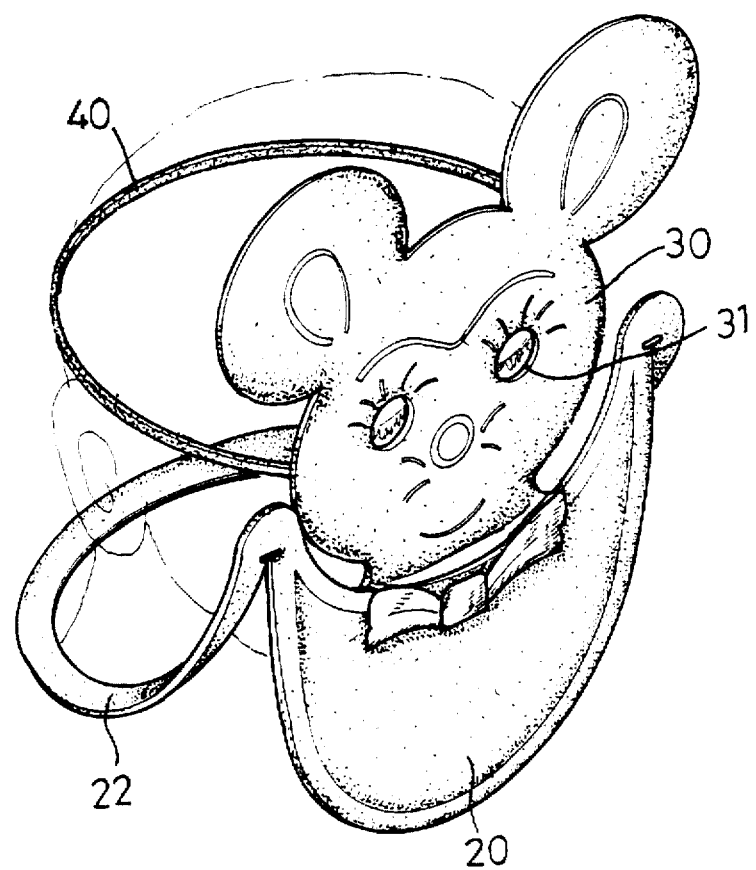
FIG. 5 is an illustrative view to show a decorative plate of the sun-visor is used as a mask.

Referring now to FIG. 4, the first plate 20 is used as a peak and the second plate 30 is a decorative plate which can be shaped as an image it such as the shown. The fastening member 22 is folded away from the first plate 20 that the sun-visor can be mounted on a wearer's head so that the first plate 20 (the peak) screens sunlight. FIG. 5 shows the decorative plate is used as a mask 30 by mounting the belt 40 to the wearer's head whereby the wearer can still see via the two holes 31.

The sun-visor in accordance with the present invention has an additional function as being used as a mask and can be manufactured cheaply in one piece. The sun-visor can be manufactured from various kinds of material when needed, such as plastic or paper board. The first plate 20 and/or the second plate 30 also can be transparent.

Although the invention has been explained in relation to its preferred embodiment, it is to be understood that many other possible modifications and variations can be made without departing from the spirit and scope of the invention as hereinafter claimed.

What is claimed is:

1. A sun-visor comprising:

a first plate having a curved inner side and a curved slit defined therethrough near an outer side thereof so as to form a curved fastening member foldably connected to two ends of said first plate;

a second plate extending from said curved inner side of said first plate, and a belt connected to two sides of said second plate.

2. The sun-visor as claimed in claim 1 wherein said second plate has two holes defined therethrough.

* * * * *